(12) United States Patent
Brabrand

(10) Patent No.: US 6,334,067 B1
(45) Date of Patent: Dec. 25, 2001

(54) METHOD AND APPARATUS FOR ASSISTING PERCUTANEOUS COMPUTED TOMOGRAPHY-GUIDED SURGICAL ACTIVITY

(75) Inventor: Knut Brabrand, Rasta (NO)

(73) Assignee: Neorad A/S, Oslo (NO)

( * ) Notice: Subject to any disclaimer, the term of this patent is extended or adjusted under 35 U.S.C. 154(b) by 0 days.

(21) Appl. No.: 09/487,921

(22) Filed: Jan. 19, 2000

Related U.S. Application Data

(62) Division of application No. 08/885,077, filed on Jun. 30, 1997, now Pat. No. 6,021,342.

(51) Int. Cl.[7] .............................. A61B 19/00; A61B 5/00
(52) U.S. Cl. ........................ 600/427; 600/429; 600/562
(58) Field of Search .................................... 600/411, 417, 600/427, 429, 414, 426, 562

(56) References Cited

U.S. PATENT DOCUMENTS

| 4,583,538 | 4/1986 | Onik et al. . |
| 5,590,655 | 1/1997 | Hussman . |
| 5,628,327 | 5/1997 | Unger et al. . |

FOREIGN PATENT DOCUMENTS

| 195 01 069 | 7/1996 | (DE) . |
| 0 755 660 | 1/1997 | (EP) . |

Primary Examiner—Ruth S. Smith
(74) Attorney, Agent, or Firm—Barry R. Lipsitz

(57) ABSTRACT

A method and an apparatus for assisting percutaneous computed tomography-guided surgical activity inside a human or animal body, such as withdrawal of body tissue or body liquid sample, withdrawal of excess body liquid, insertion or injection, said method for determining insertion depth, transversal insertion angle and craniocaudal insertion angle for a needle-type surgical instrument to be inserted into the human or animal body from an insertion entry point on a skin surface of said body to a target inside said body. From a first tomography image coordinate values of said entry point are determined, and from said first or a second tomography image coordinate values of said target point are determined. Based on said coordinate values values of said insertion depth, transversal insertion angle and craniocaudal insertion angle are calculated. Said calculated values are applied to an instrument insertion guiding apparatus positioned adjacent said body in no physical contact therewith, said apparatus having a laser which provides a laser beam, manipulating adjustment means on said apparatus to let the laser beam assume the values of transversal insertion angle and craniocaudal insertion angle and to let the laser beam point at the entry point. The instrument with a needle pointed end thereof is located at said entry point and a longitudinal axis of the instrument is aligned with said laser beam, the aligning being made by letting a distal end face of said instrument be pointed at by said laser beam.

21 Claims, 14 Drawing Sheets

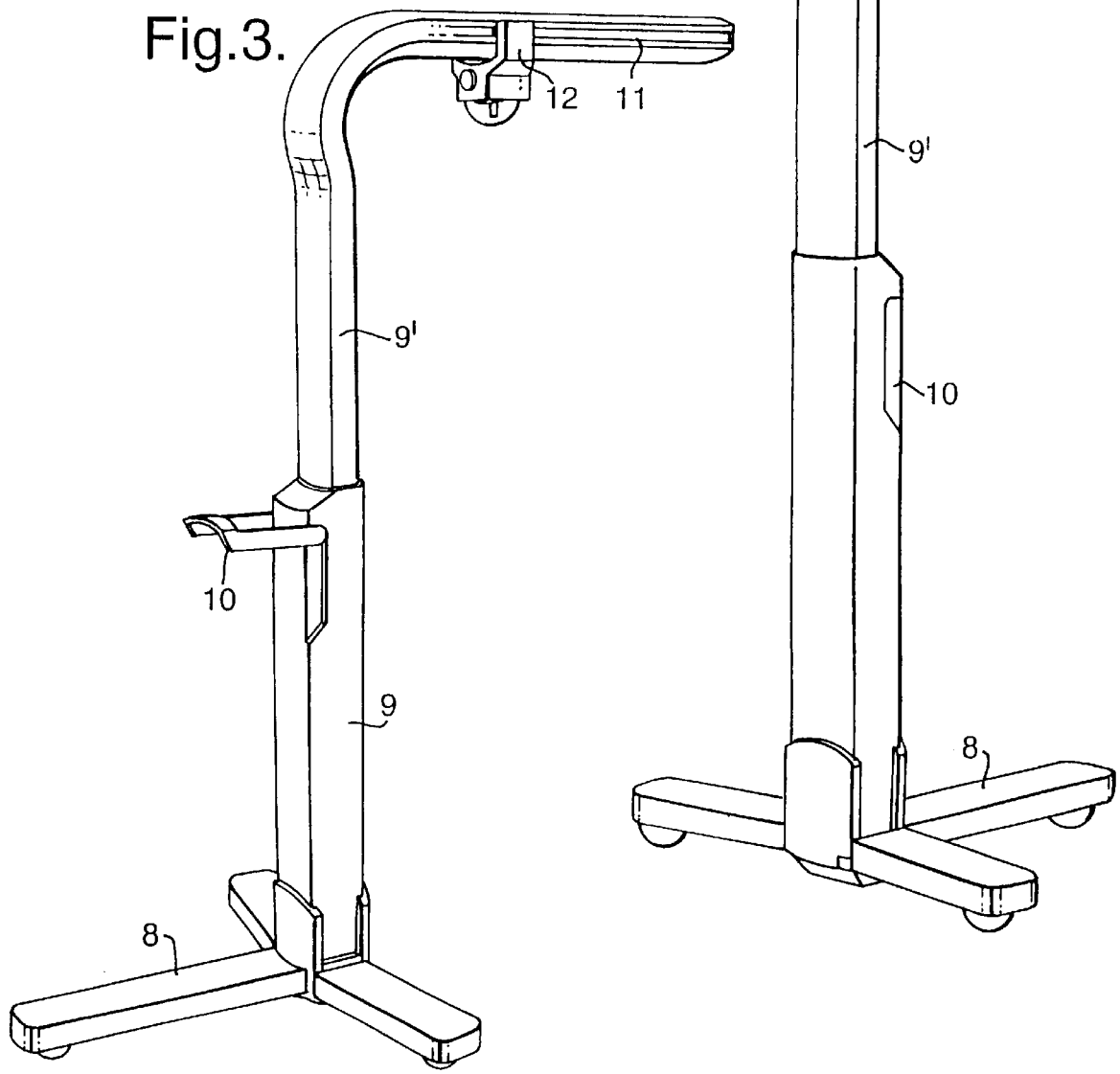

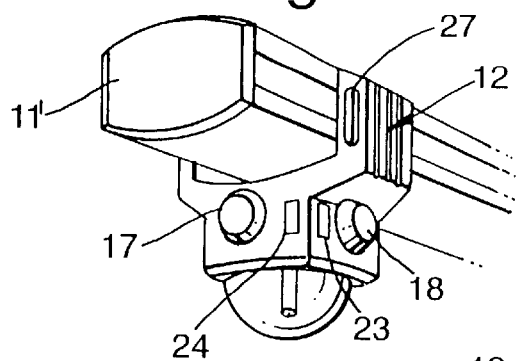
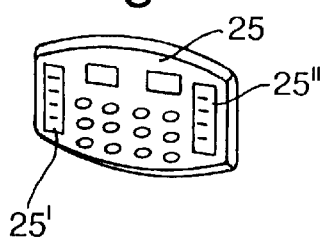
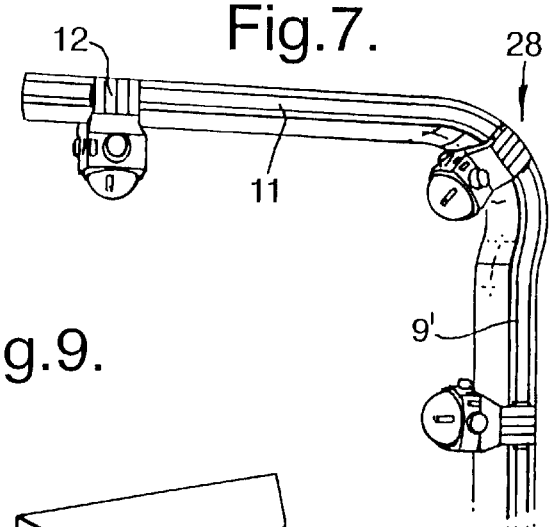
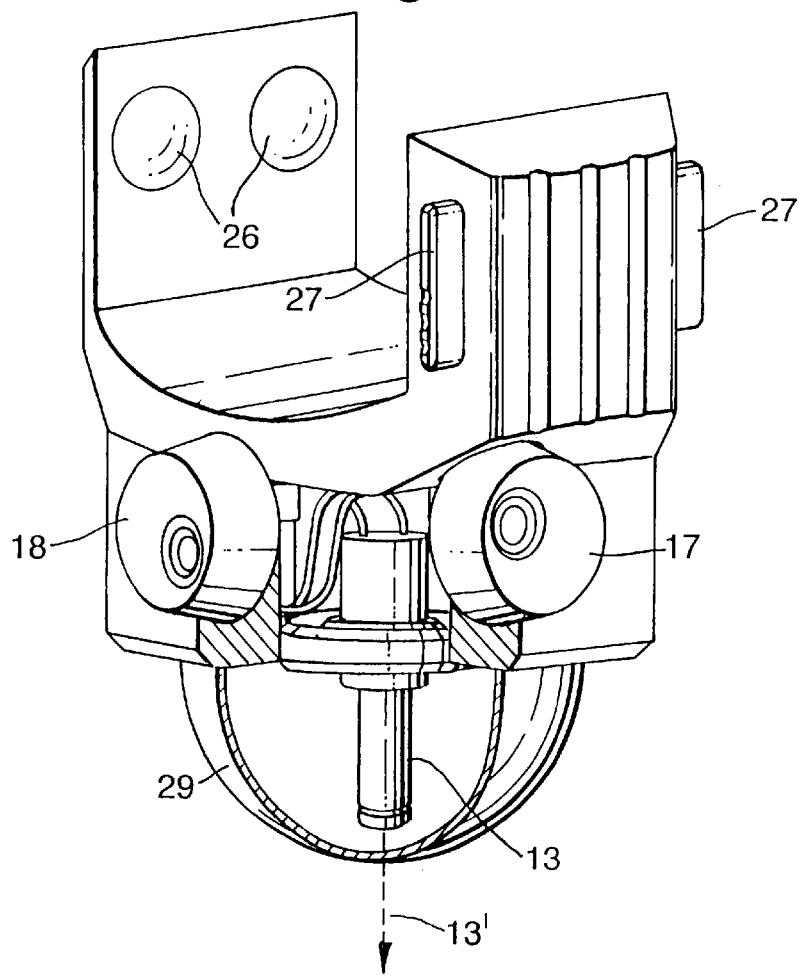

T : $(x_1, y_1, z_1)$
I : $(x_2, y_2, z_2)$

T : $(x_1, y_1, z_1)$
I : $(x_3, y_3, z_3)$

METHOD AND APPARATUS FOR ASSISTING PERCUTANEOUS COMPUTED TOMOGRAPHY-GUIDED SURGICAL ACTIVITY

This application is a divisional of U.S. patent application Ser. No. 08/885,077 filed Jun. 30, 1997 now U.S. Pat. No. 6,021,342.

The present invention relates to a method and an apparatus for assisting percutaneous computed tomography-guided surgical activity inside a human or animal body, such as withdrawal of body tissue or body liquid sample, withdrawal of excess body liquid, insertion or injection. The method is intended for determining insertion depth, transversal insertion angle and craniocaudal insertion angle for a needle-type surgical instrument to be inserted into the human or animal body from an insertion entry point on a skin surface of said body to a target inside said body. Said apparatus is related to said surgical activity when there is used a needle-type surgical instrument to be inserted into the human or animal body from an insertion entry point on a skin surface of said body to a target inside said body.

BACKGROUND OF THE INVENTION

Computed tomography (CT) is an X-ray examination method whereby sectional images, so-called slices, are taken of the body of a patient by letting an X-ray tube device rotate 360 degrees about the patient. The patient is located on a moveable table which moves in incremental steps slowly through an opening or tunnel where the X-ray tube device rotates about the tunnel. The body of the patient is thereby sectioned by a CT computer approximately like cutting a bread in slices. Each of these slices are then viewed by an operator on a display. The slice images are taken at right angles to the longitudinal axis of the patient body, and each image has a number corresponding to an address along the longitudinal axis (z-axis). It is possible to select both the thickness of the slices and the interdistance between the slices. The normal slice thickness is 7 or 10 millimetres thickness edge-to-edge.

It is sometimes necessary to introduce a thin instrument needle into a patient and towards a region to be investigated, and e.g. remove some tissue cells in order to establish whether e.g. a malignant tumour is present. If such tumour is large and close to the skin surface, such biopsy procedure is normally not complicated. However, if the tumour is small and/or lies deeply inside the body, it will be appreciated that it can be very difficult to hit the target tumour exactly with the needle.

Present day practice is that first, a series of computed tomography slice images are made of the patient. Thereafter, the various images to be shown on the display are searched until an image is found where the tumour is clearly shown.

Thereafter, an electronic marking is made on the display corresponding to the spot on the skin where it is desired to have the point of insertion, e.g. 5 centimetres to the right of a centreline. Thereafter, the patient table is moved to the address or table position on the image in question, and by means of a guide light, a line is drawn transversely of the body of the patient, corresponding to the longitudinal axis address of the image in question. It is then measured by means of a ruler 5 centimetres to right from the centreline, and a marking is made thereat on the body. At that marking there is placed a small metal indicator, e.g. the point of a syringe which is attached to the skin by means of adhesive tape and parallel to the longitudinal axis of the patient body.

Again, the image in question is taken, and at this occasion the metal indicator will appear on the image at the intended point of insertion, and it is thereby possible to check that the point of insertion corresponds to that which was intended.

The next step is to place two electronic crosses on the display, one at the point of insertion and one at the tumour. The CT computer will then calculate the distance between the two points and the angle therebetween. The distance may e.g. be 7.5 cm, and the angle e.g. 21.5 degrees to the right relative to the vertical. Local anaesthetics is applied to the region of the point of insertion, and an instrument needle is thereafter moved 7.5 cm into the patient body.

One substantial drawback of such procedure is that the proper angle when inserting the needle has to be determined by the radiologist more or less by eye measure. Using devices which can be placed on the human body and in physical contact with the instrument and its needle are cumbersome in use, inaccurate and must be thoroughly desinfected after used or be of a single use type. Such devices are therefore expensive in use, and the risk of infection is present, unless absolute sterile conditions are present during the repeated attempts to hit the target, e.g. a tumour.

Therefore, in practice, the radiologist more than often simply determines the angle of the insertion of the needle based on eye measure judgement only. As will be appreciated, it is not at all easy to introduce a needle at an exact angle of 21.5 degrees based on eye measure only. In addition, the insertion is to be made in a plane exactly 90 degrees to the longitudinal axis of the patient body. Thus, using the present day method of so-called free-hand puncture it is frequently required to make several puncture attempts before the target is hit. After each puncture attempt, new slice images must be taken to check whether the needle point of the instrument has hit the target or not. Sometimes, it is experienced that the instrument needle has not been introduced into the body in plane 90 degrees to the longitudinal axis of the patient body, and the needle can thereby have moved out of the slice plane. It will be recognised by any surgeon that difficult puncture operations are extremely time-consuming, and in the worst case may take more than an hour. This yields an increased risk of complications, such as internal bleedings, in addition to the obvious discomfort of the patient. Further, a computed tomography machine is a very expensive device which costs approximately one million US dollars or more. Thus, the cost of using a machine per time unit is important. Therefore, this is more than often a problem in the medical examination process within a hospital, and time consuming attempts to hit the target within the patient body may occupy the CT-machine for an unacceptable long period of time.

In order to solve the problem of introducing the instrument needle into the patient body at a correct angle, some hospitals use different types of puncture accessories, both mechanical and optical. In practice, they are not widely used, simply because their operation is somewhat cumbersome.

From the prior art there are known many methods and apparatus for assisting percutaneous computed tomography-guided surgical activity inside a human or animal body. Many apparatus and methods, however, strongly rely on the apparatus being clamped onto the human body, e.g. the head of a human, such as described e.g. in U.S. Pat. No. 5,116, 344. Other devices such as that described in Austrian patent 387903 rely on the apparatus being attached to the human body at the insertion point and with the needle type surgical instrument extending through a guide tube of the apparatus. Such an apparatus requires either thorough cleaning after use or that the apparatus is simply a single-use apparatus, which makes it rather expensive.

U.S. Pat. No. 4,733,661 relates to a hand-held apparatus for insertion of the surgical instrument, but is difficult to use, because the surgeon must use one hand on the apparatus and one hand on the surgical instrument to be inserted, which may prove difficult in practice.

Also, the surgical instrument is in contact with the device and thorough cleaning of the device after use is absolutely required.

U.S. Pat. No. 5,308,352 relates to a stereotactic device supported by a frame structure over the platform on which the human or animal body is placed. The device is put into a physical contact with the body and in that position clamped to the supporting frame. Thereafter, the surgical instrument is inserted into the body through a pair of guide holes. Thus, the stereotactic device according to U.S. Pat. No. 5,308,352 also requires thorough cleaning after use, which makes it complicated and expensive for practical purposes.

A stereotactic instrument similar to that of U.S. Pat. No. 4,733,661 is also known from European patent publication 0414130. However, the same deficiencies as with other prior art devices of the same type also apply to that of European patent application 041430.

The present invention, however, is intended to provide a method and an apparatus in which the assistance in the surgical activity is based on a non-physical contact between the apparatus and the human or animal body or between the apparatus and the needle-type surgical instrument to be inserted into said body.

SUMMARY OF THE INVENTION

According to the present invention, the method comprises determining from a first tomography image co-ordinate values of said entry points related to a first tomography slice position along craniocaudal direction, and horizontal and vertical directions transversely of said craniocaudal direction at said first position, determining from said first or a second tomography image co-ordinate values of said target point related to said first or a second tomography slice position along craniocaudal direction, and horizontal and vertical directions transversely of said craniocaudal direction at said first or second position, and calculating from said first and second co-ordinate values through principle of trigonometry values of said insertion depth, transversal insertion angle and craniocaudal insertion angle.

Further, the method according to the invention comprises applying said values of said transversal insertion angle and craniocaudal insertion angle to an instrument insertion guiding apparatus positioned adjacent to said body in no physical contact therewith, said apparatus having a laser which provides a laser beam and manipulating adjustment means on said apparatus to let said laser beam assume said values of transversal insertion angle and craniocaudal insertion angle and to let said laser beam point at said entry point.

Further, the method comprises locating said instrument with a needle pointed end thereof at said entry point and aligning a longitudinal axis of said instrument with said laser beam. Said instrument will be in no physical contact with said apparatus. In order to carry out said aligning, a distal end face of the instrument is pointed at by said laser beam.

A laser carrying arm or transverse member of said apparatus is located to lie horizontally above the body at right angles to the craniocaudal direction. The laser beam can provide a spot or cross-hair like image on said distal end face.

Thus, the present method provides a non-physical contact with the human or animal body in the process of assisting percutaneous computed tomography-guided surgical activity.

The apparatus, according to the invention comprises a laser beam generator device, adjustment means physically linked with said device, said adjustment means for adjusting direction of said beam based on computed transversal insertion angle data and craniocaudal insertion angle data obtained from computed tomography slice data, said beam direction being adjustable to be coaxial with insertion direction of a needle-type surgical instrument to be inserted into the human or animal body from the insertion entry point on the skin surface of said body to the target inside said body, angle indicator means associated with said adjustment means for indication of said insertion angles, power supply means and means supporting the apparatus so as to be in no physical contact with said body.

According to a further embodiment of the apparatus, there is provided insertion angle calculating means for calculating a transversal insertion angle and craniocaudal insertion angle values based on first tomography image co-ordinate values of said entry point related to a first tomography slice position along a craniocaudal direction, and horizontal and vertical directions transversely of said craniocaudal direction at said first position, and second tomography image co-ordinate values of said target point related to said first or a second tomography slice position along craniocaudal direction, and horizontal and vertical directions transversely of said craniocaudal direction at said first or second position.

Further, the apparatus provides insertion depth calculating means for calculating insertion depth into said body of said surgical instrument from said first and second co-ordinate values through principles of trigonometry.

The apparatus may comprise an arm carrying said laser beam generator device, said arm being located horizontally and at right angles to the craniocaudal direction. In addition, the apparatus can be provided with an auxiliary laser beam generator device providing a vertical light plane parallel to the cranocaudal direction.

According to even a further embodiment of the apparatus, said supporting means has a base member, an upright member extending from said base member, and a transverse member or arm extending from a top region of the upright member. Further, said base member suitably rests on a floor.

As an alternative, said supporting means is attached to a bed base member forming a support for a computed tomography machine bed movable therealong and supporting said human or animal body, said supporting means having an upright member and a transverse member or arm extending from a top region of the upright member. Suitably the supporting means is slidably attached to said gantry means to be slidable in a craniocaudal direction.

According to a further alternative, said supporting means is suspended from a ceiling or from a top part of the CT apparatus above a movable computed tomography machine bed which supports said human or animal body, and said supporting means has a horizontally located transverse member or arm.

Said laser beam generator device is movable along said transverse member and selectively is fixable at arbitrary locations therealong.

Said device is movable along said transverse member or arm and is selectively fixable at arbitrary locations therealong.

Further, said upright member is suitably a height adjustable telescopic device.

In the said further alternative said supporting means has means for adjusting a vertical level of said transverse member or arm.

Thus, above the CT-movable table the laser beam generator device is movable along the transverse member or arm being a rail means. The laser can be angled generally in two directions, both transversely of the longitudinal axis of the patient body and in the craniocaudal direction. The rail can be installed horizontally, e.g. 1 meter above the patient and is located 90 degrees relative to the CT table longitudinal direction. The laser is movable to the left or the right of the longitudinal axis of the patient body along said rail. The rail is supported by the upright member or is suspended from a ceiling. The point of insertion on the skin is marked by use of suitable ink. The laser is set to the correct angle, i.e. the angle which has been read on the display, and is moved either to the right or the left relative to the longitudinal axis of the patient body, such that the laser light beam illuminates exactly the marked point of insertion. Adjustment along the longitudinal axis of the patient body in order to have the laser light beam hitting the point of insertion is made by driving the CT-table towards the head and/or the foot end, which operation can be made to the accuracy of millimetres.

With the present invention the skin at the point of insertion of the instrument needle is properly cleaned and the puncturing needle end is placed on the skin at the point of insertion, i.e. where the laser beam spot or cross-hair image is seen. The instrument needle is kept in such position that the laser light beam hits the rear centre face of the instrument. Thereafter, the needle is moved into the patient, simultaneously with ensuring that the laser light beam is all the time seen as a red spot or a red cross on the rear end face of the needle-type instrument. The needle is thereby introduced at the correct insertion angle. In the usual way, the insertion distance or depth has been marked on the needle by means of steristrip (sterile, narrow adhesive tape) if there is no centimetre or millimetre scale on the needle.

Any further features of the present invention will appear from the attached claims, as well as from the following description of the invention with reference to the attached drawings describing non-limitative examples of embodiments according to the present invention.

BRIEF DESCRIPTION OF THE DRAWINGS

FIGS. 3 and 4 are perspective views from opposite sides of the apparatus according to the invention.

FIGS. 6, 7 and 8 are further detailed views of the apparatus, according to the invention.

FIG. 9 is a detailed, partly cut-away view of a part of the apparatus, according to the invention.

DETAILED DESCRIPTION OF THE INVENTION

Figure 1:
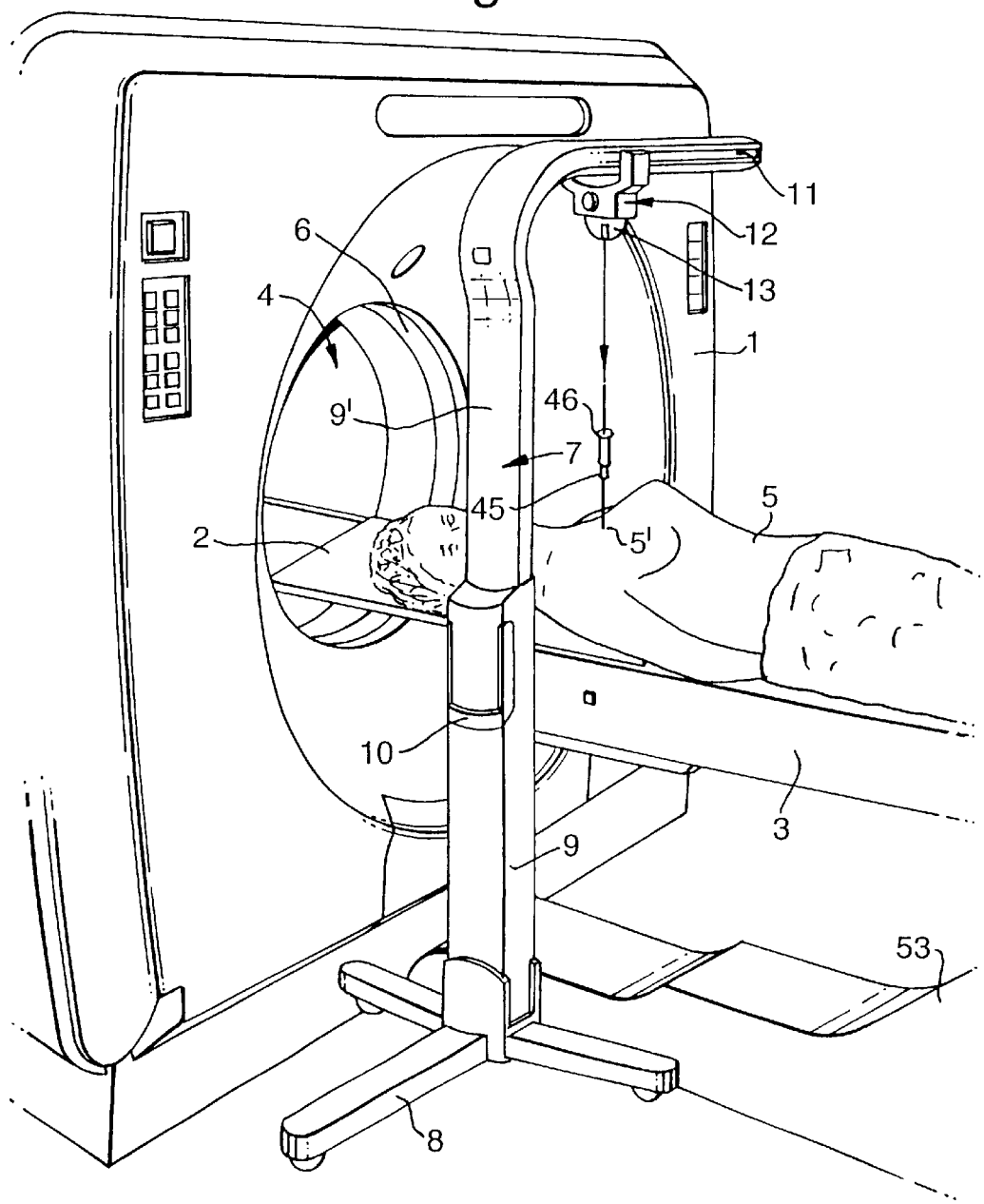
FIG. 1 illustrates an embodiment of the present device with a computed tomography apparatus.

A computed tomography apparatus, in the remaining description defined as CT apparatus (FIG. 1). The CT apparatus 1 has a patient supporting table 2 which is slidable along a support 3 having means therein for moving said table 2 at least partly through a scanner opening 4 in the apparatus 1 by means of motors inside the support 3 providing incremental movement modes of said table 2 on which a patient 5 to be examined is placed. The CT apparatus has inside in a manner known per se and not to be described further a rotary scanner moving along a circular formed slit 6 as indicated on FIG. 1.

Figure 10:
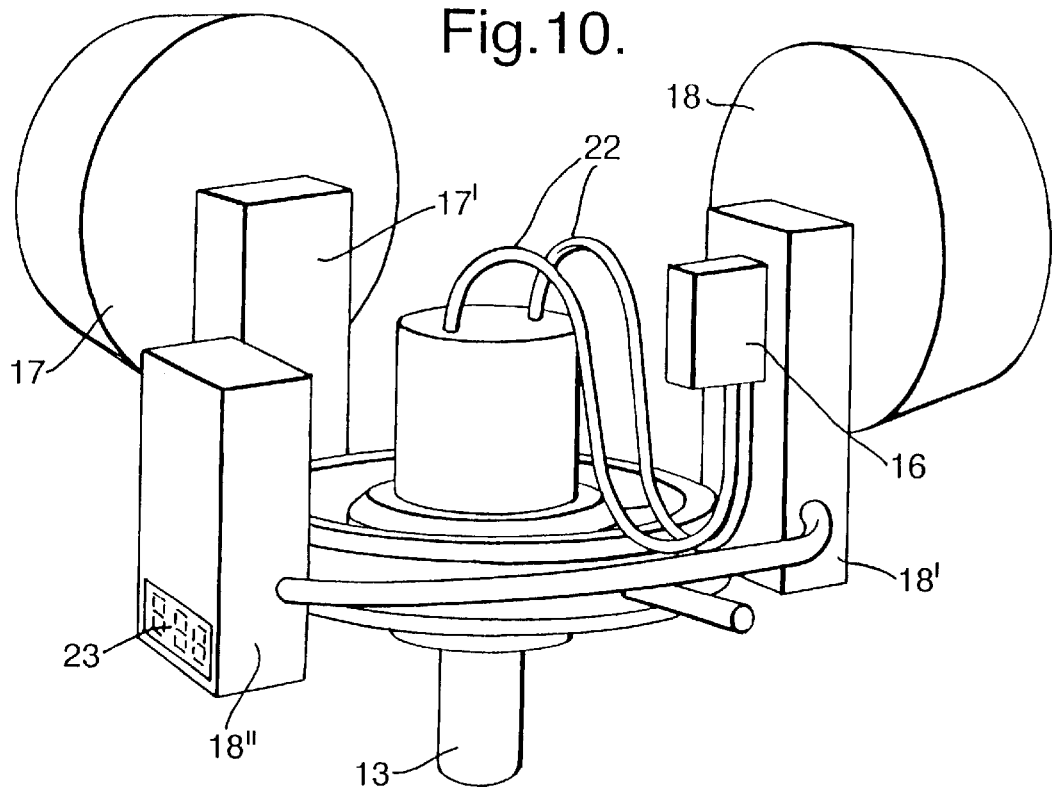
FIG. 10 is a partial schematic view of the detailed partial embodiment shown in FIG. 9.
Figure 11:
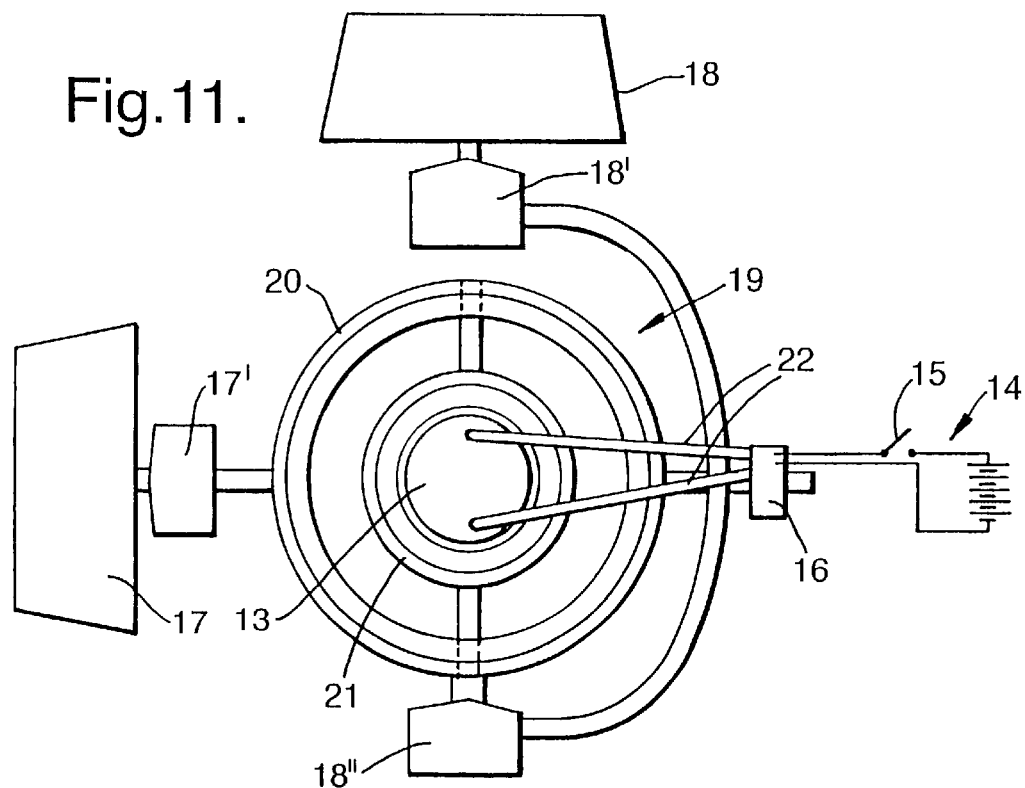
FIG. 11 is a schematic view from above of the embodiment of FIG. 10.

The apparatus for assisting percutaneous computed tomography-guided surgical activity inside the body of a human, such as the patient 5, is generally indicated by reference numeral 7. In a non-limited embodiment of the invention the apparatus 7 consists of a base member 8, upright members 9 and 9', which are preferably telescopically mounted and mutually lockable by means of a locking handle 10. Further, the apparatus 7 has a transverse member 11 extending from a top region of the upright member 9'. The apparatus 7 has a unit 12 moveable along the transverse member 11 and lockable in position there along. The unit 12 has laser beam generator device 13 including a power supply means 14 (FIG. 11) for the device 13. Said power supply means 14 has suitably an on/off switch 15. The laser beam generator device 13 has suitably a power inlet terminal 16 show in FIGS. 10–11. Based on calculations to be explained further, transverse insertion angle and craniocaudal insertion angle can be calculated. Using, e.g., turning knob 17, the transversal insertion angle to be described by a laser beam 13' can be set. Similarly, the craniocaudal insertion angle can be set for the beam 13' by means of an adjustment knob 18 (FIG. 9). The turning of the knob 17 is a movement which is transferred through a gear box 17' to a two-dimensional turning device 19 having an outer ring and inner ring which are moveable relative to each other. Thus, viewing FIG. 11 turning of knob 17 means that the laser device 13 will be moveable in the direction of the long side of the drawing sheet. Movement of the adjustment knob 18 via a first gear box 18' and a second gear box 18" will yield that the ring 21 will move relative to ring 20 in order to be able to move the laser device 13 parallel to the short side of the drawing sheet.

The gear box 17' and suitably also the gear box 18" may have angle indicators in order that an operator of the inventive apparatus may know when the set angles have been reached.

The laser beam generating device 13 receives power from the power supply 14 via connecting wires 22. A display for indication of e.g. the craniocaudal insertion angle has been schematically indicated on FIG. 10 by reference numeral 23. The angle indicator has also been shown as an example on FIG. 6. Similarly, as shown on FIG. 6, an angle indicator for the transversal insertion angle has been indicated by reference numeral 24. As indicated on FIG. 8, a calculator device 25 could form an integral part of the apparatus and e.g. be locatable on an end part of the transverse member 11, as indicated on FIG. 6 by reference numeral 11'. Based on x and y values obtained from tomography image co-ordinate values, it will be possible to calculate the transversal insertion angle and craniocaudal insertion angle and have those angle values shown on displays 25' and 25".

As shown on FIGS. 6 and 7, the unit 12 is moveable along the transverse member 11 and can be locked in any position therealong by means of locking members 26 releasable by pushing knobs 27. In a particular embodiment, it is considered possible to move the unit 12 over a transition region 28 between the transverse member 11 and the upright member 9'.

Figure 5:
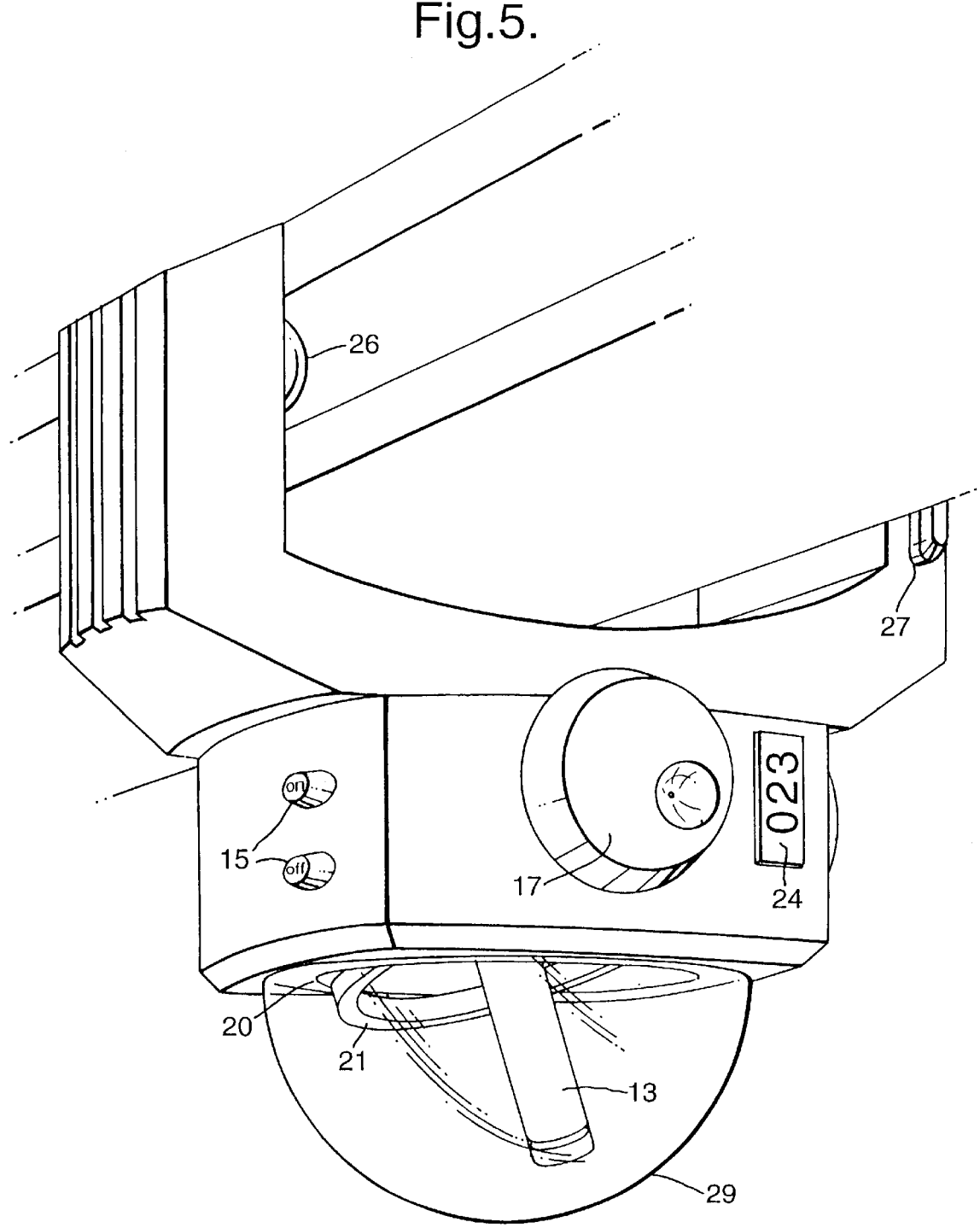
FIG. 5 is a detail of the apparatus at an enlarged scale.

Suitably, a radome 29 is located below the exit of laser beam generator device 13, said radome 29 (FIG. 5) being of a material and thickness causing little or negligible refraction of the laser beam 13 when it passes through the radome material. Suitably, the exit of the laser beam generator device 13 is close to the inner surface of the radome. The radome is primarily for protecting the laser beam generator device 13 against damage caused by accidental impacts.

Figure 2:
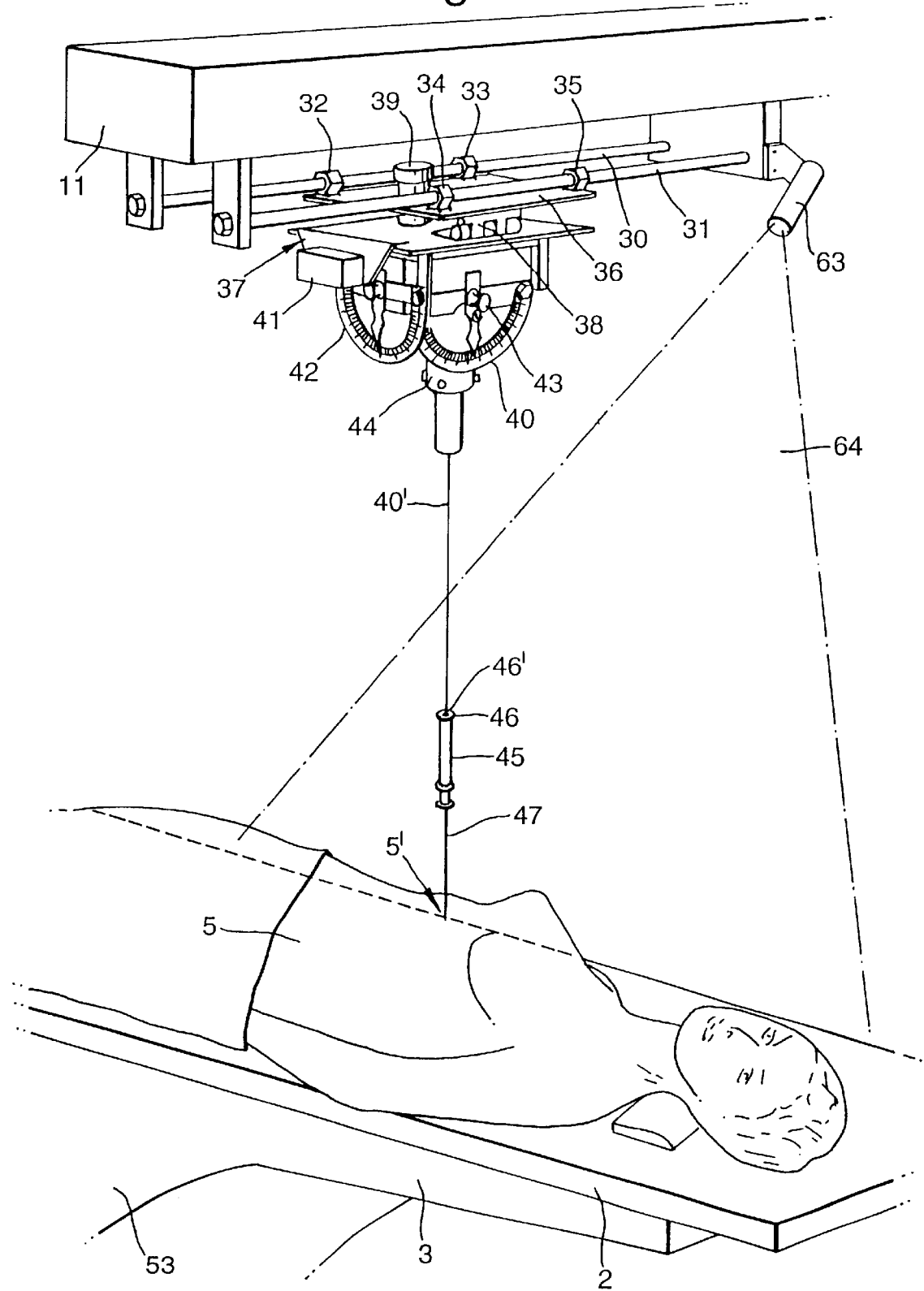
FIG. 2 is a simplified version of the apparatus according to the invention in a prototype embodiment.

A more simplified version of the apparatus, according to the invention, forming a prototype of the apparatus is shown in more detail on FIG. 2. The apparatus has a transverse top beam 11 which is connectable to an upright member 9, 9'. The transverse member 11 has suitably a pair of slide rails 30, 31 with slide shoes 32, 33, 34, 35 attached to a common plate member 36. The plate 36 is attached to a unit 37 via a hinge connection 38 and a craniocaudal angle adjustment of connection 39. The unit 38 consists of a laser beam generator device 40, suitably of the same type as denoted by reference numeral 13 in connection with the disclosure of the embodiment shown on FIGS. 1, 3–11. Further, said unit 37 has suitably a level 41 for indicating a craniocaudal insertion angle equal to 0 degrees as also indicated by an angle indicator 42. A transversal insertion angle indicator 43 is also located on unit 37 and is provided with a fixation knob 44. When the proper transversal insertion angle and craniocaudal insertion angle have been calculated, the laser beam 40' will point at the correct insertion point 5' on the body of the patient 5. The needle-type surgical instrument to be inserted into the body of the patient 5 is denoted by reference numeral 45 on FIG. 2. The instrument 45 is to be hand-held by a surgeon. At a distal end 46 of the instrument, there is located an aiming point or face 46', suitably, but not necessarily, made of a light reflective material. Thus, keeping in mind that the laser beam 40' is directed to point with correct transversal insertion angle and craniocaudal angle at the insertion point 5', inserting the instrument at the insertion point 5' and ensuring that the aiming point or face 46' is always hit by the laser beam 40', will ensure that the instrument is moved correctly into the body of the patient 5. Although the laser beam 40' may create only a light spot on the distal end 46 of the instrument, the laser beam could be of a cross-hair type, thus more readily defining a centre point on said distal end 46.

In a manner known per se the needle portion 47 of the instrument 5 has a length scale, e.g. in metric units such as centimetres, to be able to observe the correct insertion depth of needle portion 47.

Thus, by knowing the correct transversal insertion angle and the craniocaudal insertion angle, as well as the insertion depth, a safe insertion of the needle portion 47 of the instrument 45 into the body of the patient 5 can be made.

The instrument is suitable for withdrawal of body tissue or body liquid sample, withdrawal of excess body fluid, insertion or injection. In a preferred application of the present invention, the instrument is suitable for taking a body tissue or body liquid sample, e.g. known as aspiration cytology, percutaneous fine needle biopsy or surgical micro biopsy.

A most important advantage of the present invention over the prior art is the feature of the apparatus being in physical non-contact with the instrument to be inserted into the patient's body. This is clearly seen from FIG. 1. In turn, this means that the apparatus, according to the invention does not require any disinfection cleaning operation after a biopsy has been performed, contrary to the prior art apparatus for assisting percutaneous computed tomography-guided surgical activity related to insertion of a needle-type surgical instrument into a human or animal body. A further advantage over the prior art is that the operator may use both hands while introducing the needle, i.e. the operator does not have to support the instrument with one hand.

Calculation of transversal insertion angle and craniocaudal insertion angle and the combination thereof to obtain the correct direction of insertion is now to be further described with reference to FIGS. 12–17.

Figure 12:
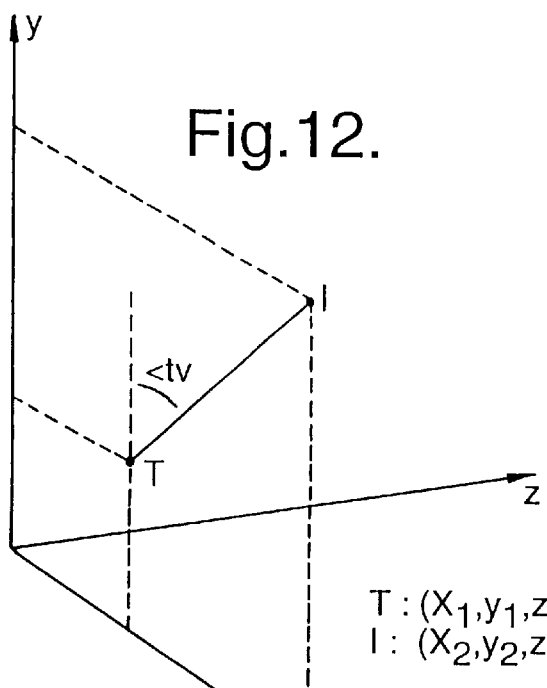
FIG. 12 is a x, y, z diagram to illustrate insertion entry point and target in a single plane.
Figure 14:
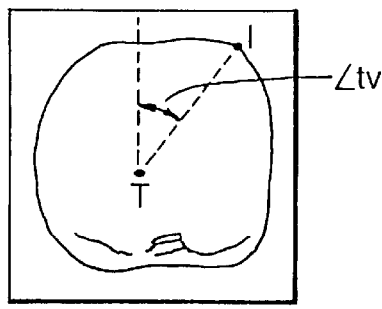
FIG. 14 is a display image of an insertion entry point and target in a single plane.

The insertion point is generally denoted by I, and the target, e.g. a malignant tumour is denoted by T. In the simple example as illustrated by FIGS. 12 and 14, the insertion of the instrument 45 and its needle portion 47 is determined to be made in a single tomography image plane with co-ordinates for the target and the insertion point denoted by co-ordinates x1, y1 and x2, y2, respectively. The angle can be calculated on a separate calculating device based on the co-ordinate values or simply be read off from the tomography image viewing screen which suitably has cursor means to connect said co-ordinates on the screen and thereby determine the angle of the cursor relative to the vertical.

Figure 13:
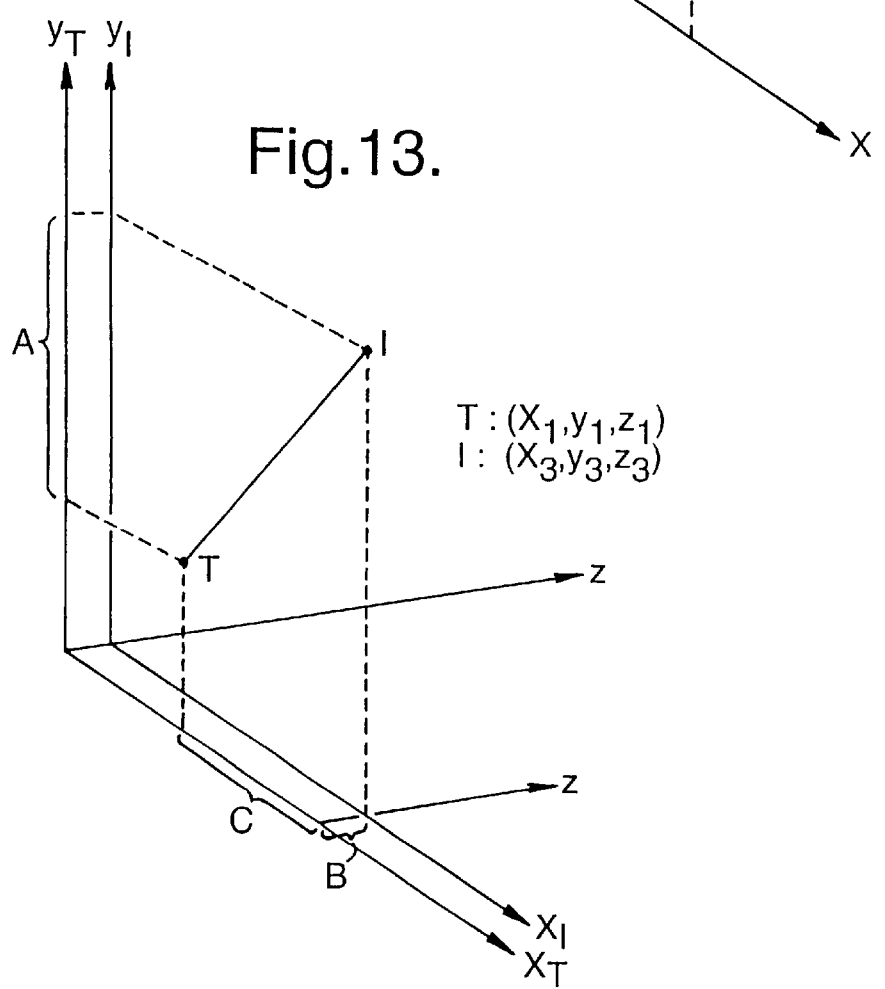
FIG. 13 is an x, y, z diagram illustrating insertion entry point in one plane and a target inside the body in another, parallel plane.
Figure 15A:
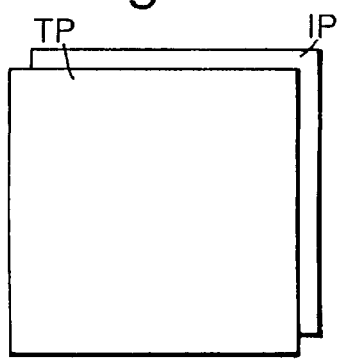
FIGS. 15a, 15b, and 15c illustrate insertion entry point and target in different planes, as indicated in FIG. 13.
Figure 15B:
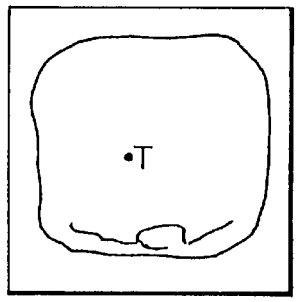
Figure 15C:
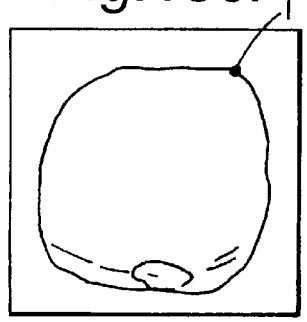

In the particular case where it is difficult to let the needle portion 47 of the instrument 45 move in a single tomography image slice plane, simply due to internal organs having risk of being punctured by the needle or be damaged or cause internal bleeding or other damages, it is more than often required to have the target in a first tomography image slice plane TP (xT, yT, zT) and the insertion point in a parallel tomography image slice plane IP, such as schematically shown on FIG. 13 as well as on FIGS. 15a, 15b and 15c. Again, the target is given the co-ordinates x1, y1, z1, z being the direction of the movement of the table 2. The insertion point is denoted by the co-ordinates x3, y3, z3. Thus, the purpose of understanding the calculation below and with reference to FIG. 17, A=y3−y1, B=z3−z1, and C=x3−x1. Thus, with reference to FIG. 7, the following calculations can be made.

$$D=\sqrt{A^2+B^2}$$

$$D^2=A^2+B^2$$

$$\tan L_{TV} = \frac{|C|}{|D|}$$

$$L_{TV} = \tan^{-1}\frac{|C|}{|D|}$$

$L_{CC}$:

$$\tan L_{CC} = \frac{|A|}{|B|}$$

$$L_{CC} = \tan^{-1}\frac{|A|}{|B|}$$

Insertion Depth $S = \sqrt{C^2 + D^2}$

Thus, by turning the proper adjustment means for transversal insertion angle and craniocaudal angle to obtain the composite direction of insertion, as well as the insertion depth, a safe insertion procedure is obtained. Naturally, it will be important to carefully check in a step-by-step fashion, how the insertion proceeds by taking repeated sets of tomography image slices.

Figure 16:
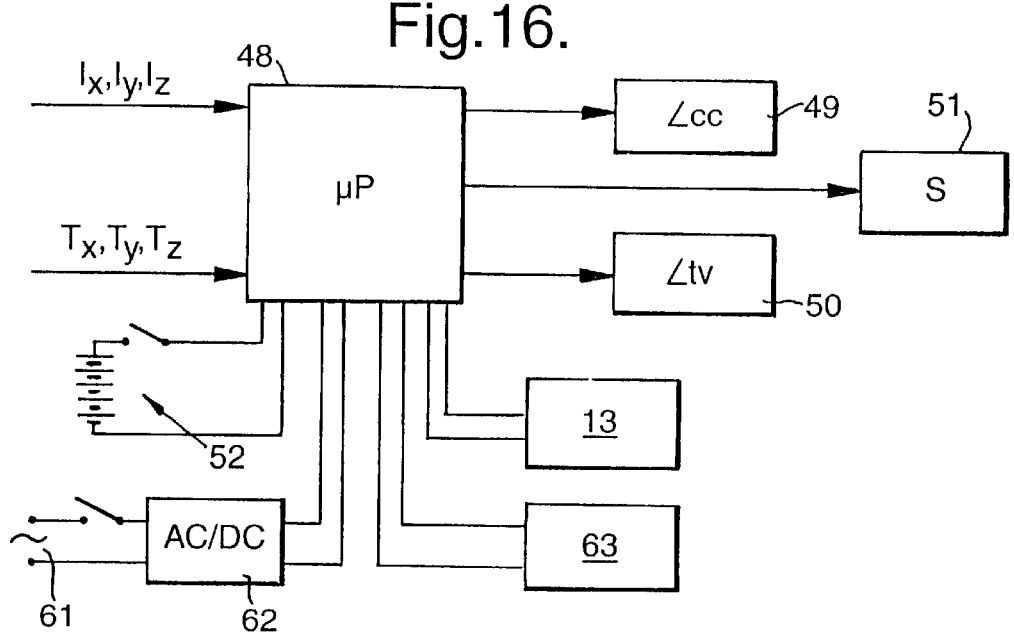
FIG. 16 is a simplified block diagram of a device for calculating transversal insertion angle, craniocaudal insertion angle and insertion depth.
Figure 17:
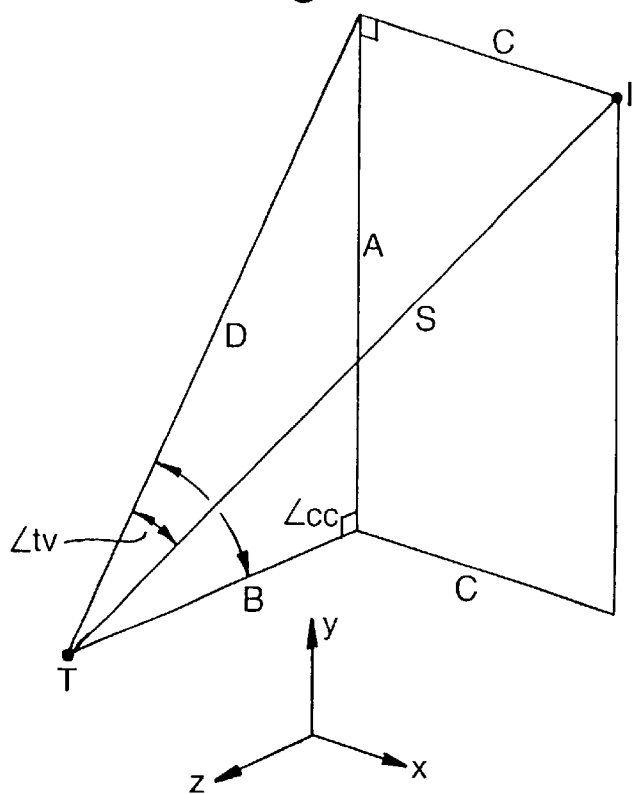
FIG. 17 is an enlarged diagram for understanding the mathematics of a calculating transversal insertion angle, craniocaudal angle and insertion depth.

On FIG. 16 there is shown in a simplified block diagram form a micro processor 48 and at the outputs therefrom displays 49 and 50 for showing the computed craniocaudal insertion angle and the transversal insertion angle, respectively, as well as a display 51 for showing the insertion depth. The microprocessor 48 calculates the appropriate insertion angle values and insertion depth value based on the co-ordinates of the proposed insertion point 5', denoted by co-ordinates Ix, Iy, Iz, and the co-ordinates of the target T, denoted by co-ordinates Tx, Ty, Tz.

In order to make sure that the transverse member or arm 11; 57; 60 is located exactly at right angle to the craniocaudal direction, the apparatus is provided with an auxiliary laser beam generator device 63 providing a light plane 64 parallel to said craniocaudal direction. As shown on FIG. 2, the plane 64 will hit and lie along the bed 2, thus indicating that the arm 11 is transversely of the craniocaudal direction.

The microprocessor 48, its displays 49, 50, 51 and the laser generator devices 13 and 63 are powered from a power supply 52. As an alternative to battery operation 52, the apparatus may be powered from the mains 61 via an AC to DC converter 62, said DC convertor e.g. delivering 12V DC or 24V DC.

Figure 18:
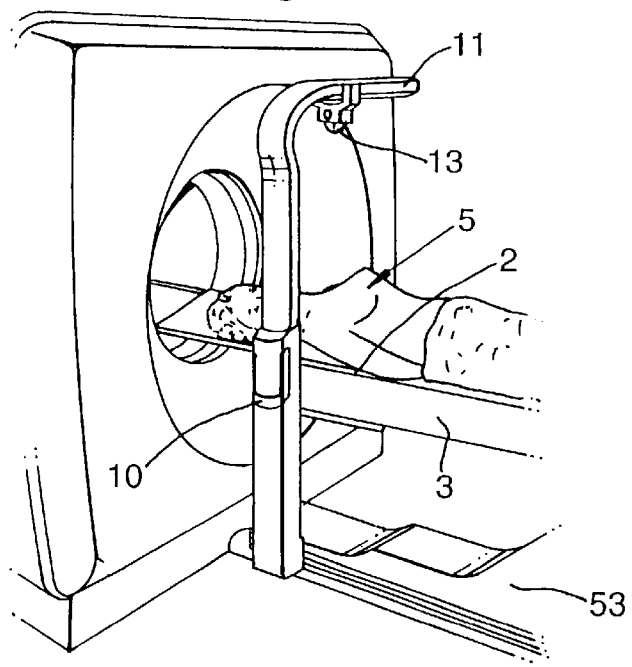
FIGS. 18–20 illustrate alternative ways of mechanically supporting the device, according to the invention.

Although, the supporting device may be of a type located on a floor, with reference to FIG. 18, an alternative is to slidably attach the apparatus supporting device to a bed or table base member 53 which supports the computed tomography (CT) machine patient supporting movable table or bed 2. Said supporting device may have a telescopic vertical adjustment means 10. The laser beam generator device 13 is movable along said transverse member or arm 11 as described before.

Figure 19:
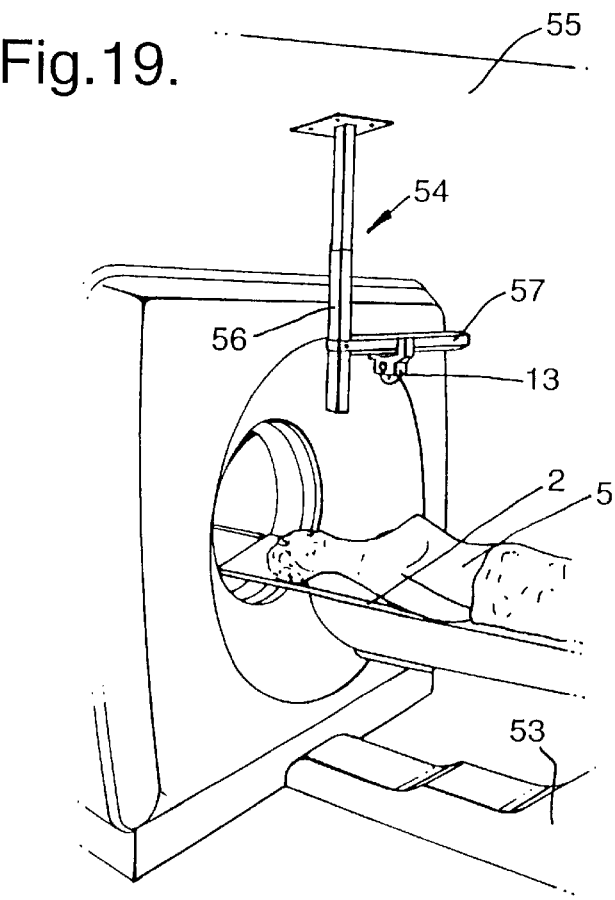
Figure 20:
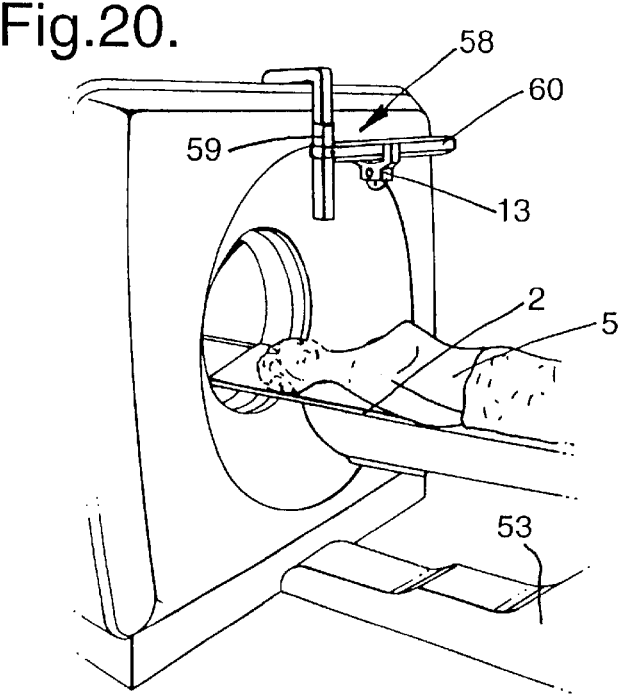

In the further alternative, with reference to FIG. 19, an apparatus supporting device 54 is suspended from a ceiling 55 above said patient supporting movable table or bed 2. The supporting device 54 may have means, e.g. telescopic vertical adjustment means 56 for adjusting the level of a transverse member or arm 57 above the human or animal body 5. The laser beam generator device is movable along said transverse member or arm 57.

In a still further alternative and with reference to FIG. 19, an apparatus supporting device 58 is suspended from a top region on the CT apparatus 1. The supporting device 58 may have means, e.g. telescopic vertical adjustment means 59 for adjusting the level of a transverse member or arm 60, above the human or animal body 5. The laser beam generator device 13 is movable along said transverse member or arm 60.

In order to more fully appreciate the importance of the present invention, reference is now directed to attached FIGS. 21a, 21b, FIG. 22 and FIGS. 23a, 23b, 23c, 23d and 23e.

Figure 21A:
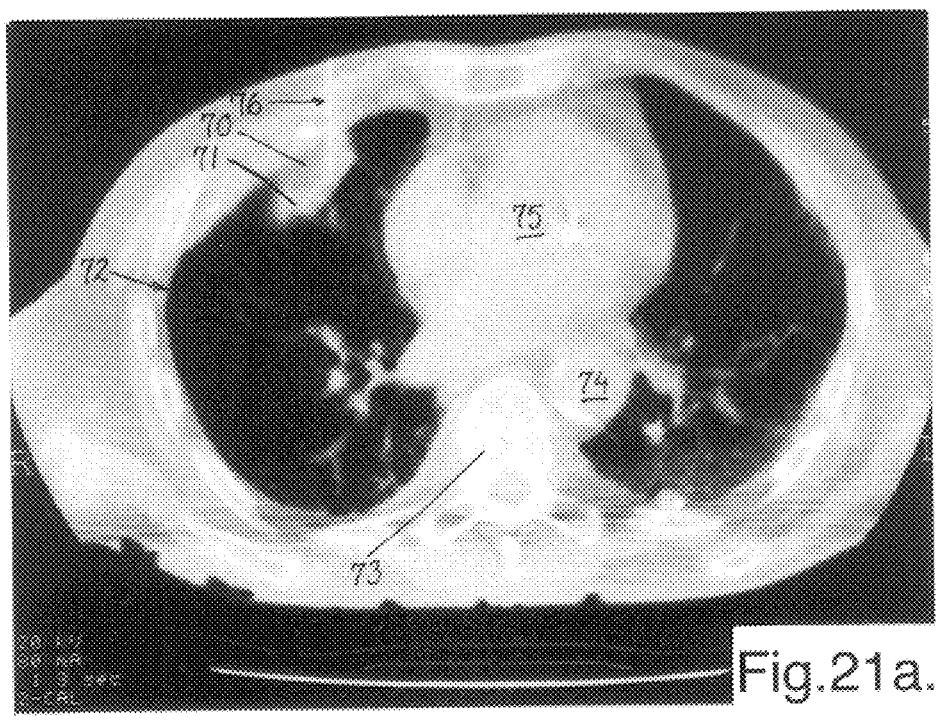
FIGS. 21a and b and FIG. 22 are CT-slices of a first medical case with traditional biopsy technique.
Figure 21B:
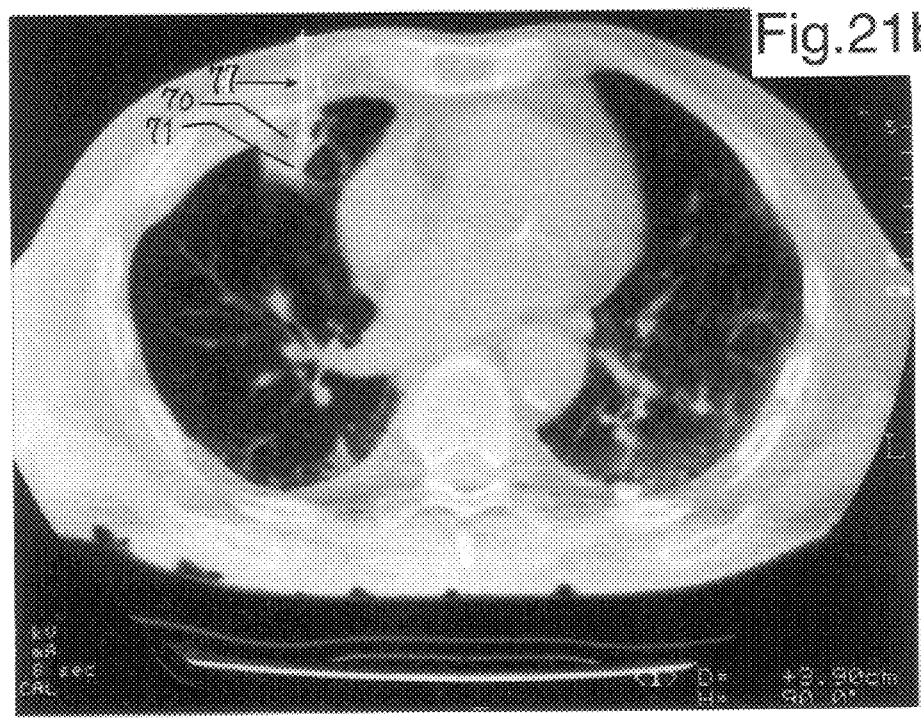

In FIGS. 21a and 21b are shown a first medical case showing a tumour having a liquid part 70 and a solid tissue part 71. As seen, the tumour is associated with the right lung 72 of the patient. For reference the spine is denoted by reference numeral 73 and the aorta by reference numeral 74. Further, the heart is denoted by reference numeral 75.

In order to perform a biopsy, the needle part of the biopsy instrument, as denoted by reference numeral 76 is to be inserted into the solid tissue of the tumour. As noted from FIG. 21b the distance required for insertion and the angle of insertion is denoted by the cursor 77. The CT slice image and evaluation thereof indicates that the insertion angle is to be 90 degrees and the insertion depth to be 3.90 cm.

With such short insertion depth and a well defined insertion angle, the biopsy is fairly straight forward to perform, even with prior art biopsy techniques.

Figure 22:
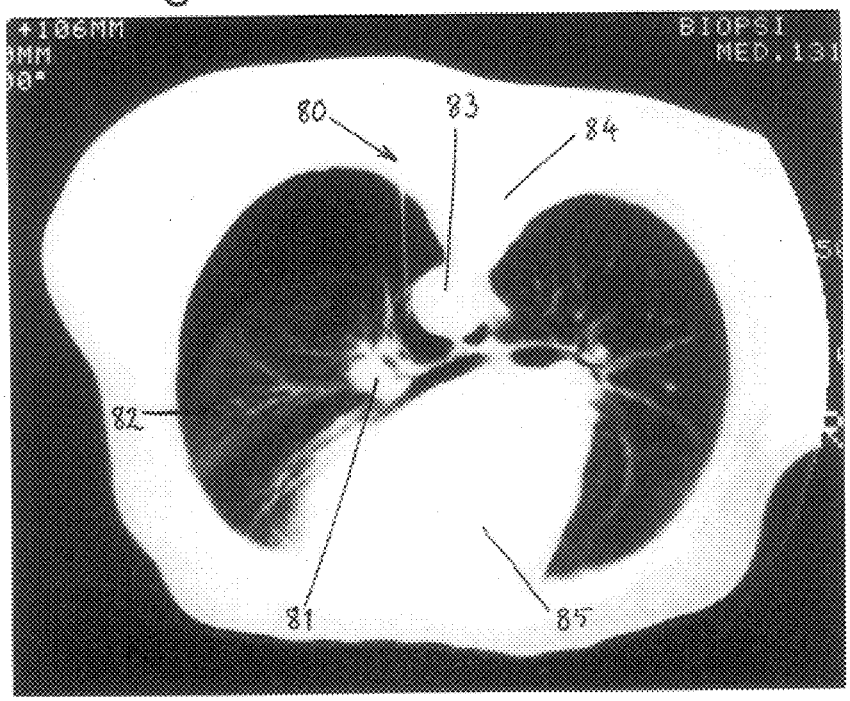

However, a more complicated and true case, medical case number two, is shown on FIG. 22. This particular case, using the prior art free-hand technique and aiming the biopsy instrument using eye measures, clearly indicates the severe risks which are imposed on patient during biopsy sample taking. In this particular case an attempt has been made to hit with the biopsy instrument needle 80 a tumour 81 located in the left lung 82. As a complication in the biopsy operation, the operator has managed to puncture the lung which has therefore partly collapsed. The image shown on FIG. 22 does not represent the first insertion of the biopsy needle 80. A repeated insertion is represented by FIG. 22 and, as shown, the needle has unintentionally passed very close to the aorta 83, with a very narrow margin. If the aorta had been punctured, a serious bleeding could have occurred. For reference, the spine has been indicated by reference numeral 84 and the heart by reference numeral 85.

The medical case of FIG. 22 clearly indicates that insertion angle of the biopsy instrument as well as insertion depth in many cases is highly critical.

It will be appreciated that using the method and apparatus of the present invention could all together have avoided the dangerous situation shown with reference to FIG. 22.

A third medical case, represented by FIGS. 23a–23e is now to be described very briefly, the biopsy using the technique according to the present invention.

In order to more fully understand the CT slice images, reference 90 denotes a rib. The left kidney is denoted by reference 91. Aorta is denoted by reference 92. Interior vena cava is denoted by reference 93. The liver is denoted by reference 94. The medical situation is that the patient has a collection of liquid in the pancreas, as denoted by reference numeral 95. Situation of post-pancreatitis is denoted by reference numeral 96. Further, pseudo-cysts are denoted by reference numeral 97. As shown on the images of FIG. 23 it was a prime object to remove the large collection of liquid within the pancreas and in particular in the pseudo-cysts, as shown on FIG. 23d. It will be appreciated that not only is the insertion depth calculation critical, but the insertion angles are highly critical, in particular with such a long biopsy needle or cannula to be used. Notably and as clearly shown on FIG. 23d and 23e, the needle or cannula, as indicated by reference numeral 98 is extremely long, almost the cross sectional width of the human body at the location of the CT slice image. Without the aid of the present method and apparatus, a puncture procedure as shown would take very long time and involve high risks of not hitting the target properly. Thus, with further reference to FIG. 23 the CT slice images clearly indicate a very complicated puncture of a series of liquid collections in the pancreas where a very long needle 98 has been inserted from the left side of the abdomen transversally towards the right. In the particular case shown, the patient was lying on the right side. On FIG. 23b the needle has been inserted at a correct angle and a control CT slice has been made to check that the needle is on a right path. The fact that the complete needle is shown indicates that the insertion has been made exactly in the transversal plane being the same as the CT slice image plane.

Figure 23A:
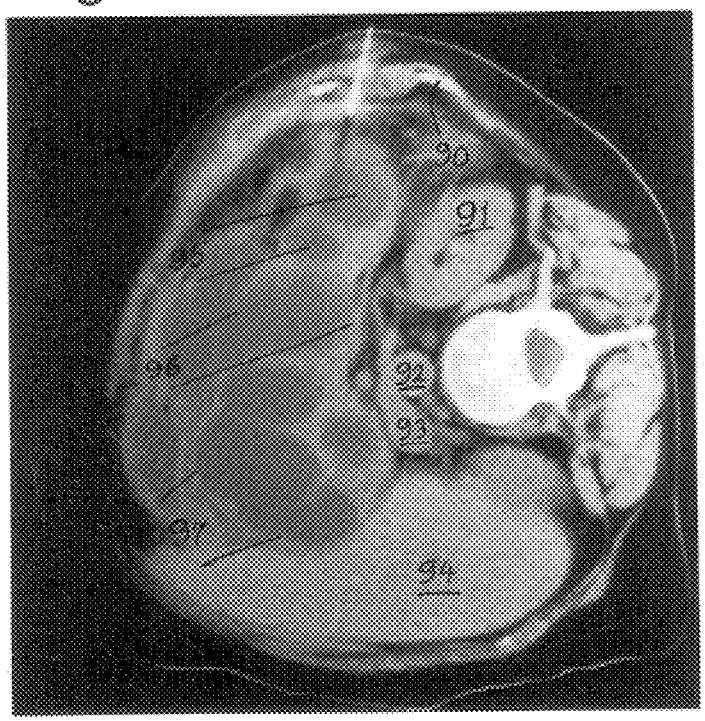
FIGS. 23a, 23b, 23c, 23d and 23e are CT-slices of a third medical case using the method and apparatus of the present invention.
Figure 23B:
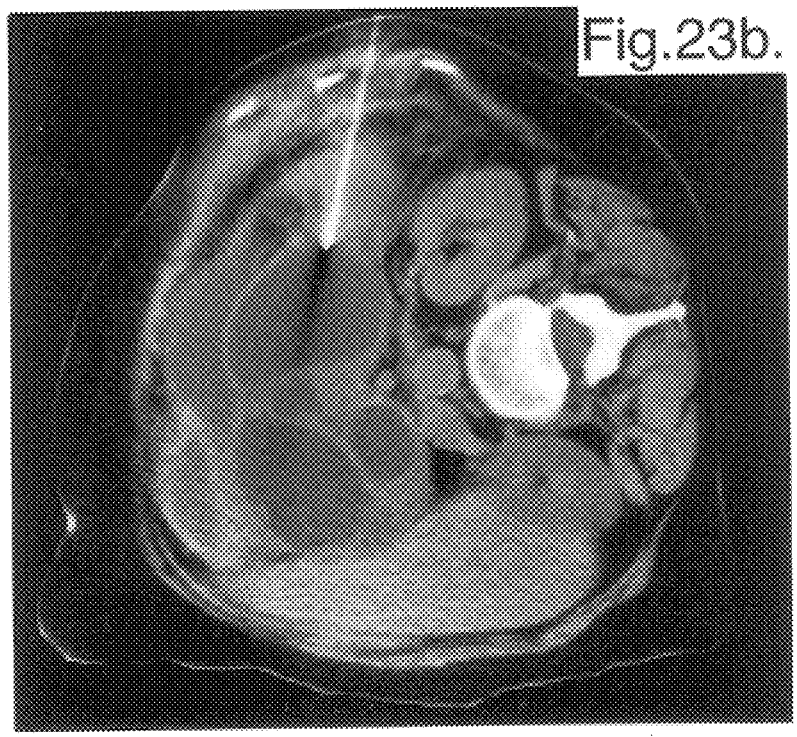
Figure 23C:
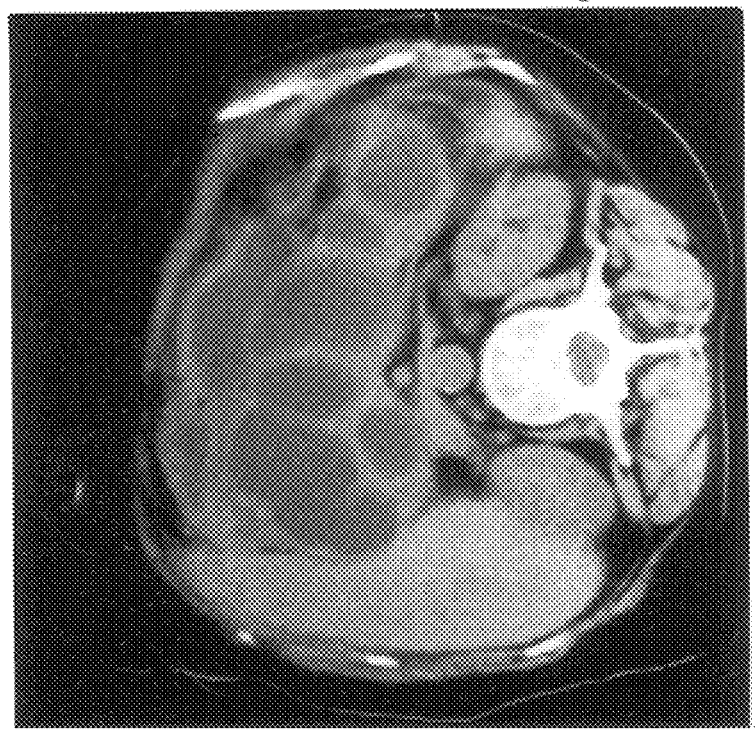
Figure 23D:
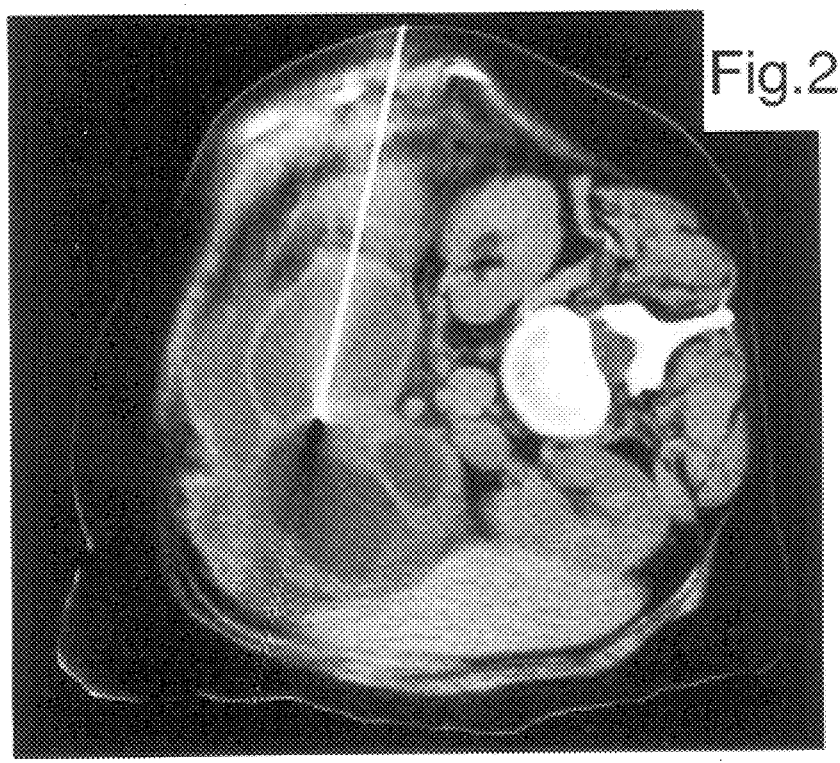

FIG. 23d indicates the needle 98 being moved further in, and the path of the needle is still a correct one. A further advancement of the needle to the liquid collection to the far right of the patient, (next to the liver 94) is shown on FIG. 23e.

Figure 23E:
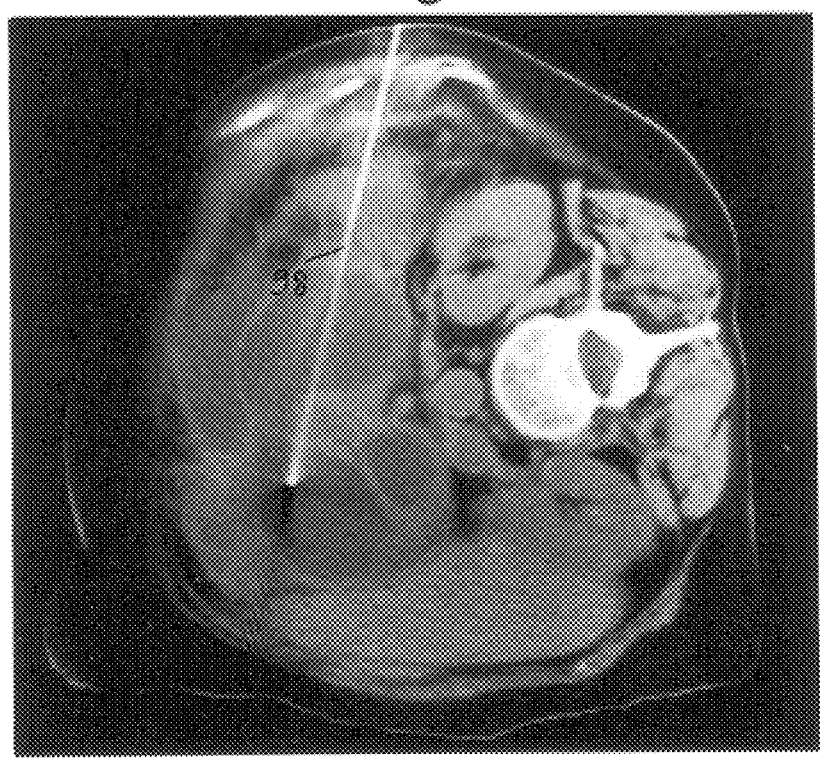

After the needle 98 hit the target shown on FIG. 23e, a thin wire was inserted through the needle to be a pilot wire for a thin tube to be inserted into the human body over the steel wire. The tube (not shown) was for draining the liquid in the pancreas.

Having described my invention, I claim:

1. A method for assisting percutaneous computed tomography-guided surgical activity inside a human or animal body, said method for determining insertion depth, transverse insertion angle and craniocaudal insertion angle for a needle-type surgical instrument to be inserted into the human or animal body from an insertion entry point on a skin surface of said body to a target inside said body, comprising:

determining from a first tomography image first coordinate values for said entry point related to a first tomography slice position along craniocaudal direction, and horizontal and vertical directions transversely of said craniocaudal direction at said first position, determining from a second tomography image second coordinate values for said target point related to a second tomography slice position along craniocaudal direction, and horizontal and vertical directions transversely of said craniocaudal direction at said second position, calculating from said first and second coordinate values through principle of trigonometry values of said insertion depth, transverse insertion angle and craniocaudal insertion angle, and said transverse insertion angle value, said craniocaudal insertion angle value, said first coordinate values, and said second coordinate values defining a direction of insertion and insertion depth from said entry point.

2. The method according to claim 1, further comprising applying said values of said transverse insertion angle and craniocaudal insertion angle to an instrument insertion guiding apparatus positioned adjacent to said body in no physical contact therewith, said apparatus having a laser which provides a laser beam, manipulating adjustment means on said apparatus to let said laser beam assume said values of transversal insertion angle and craniocaudal insertion angle and to let said laser beam point at said entry point in said defined insertion direction.

3. The method according to claim 2, further comprising locating said instrument with a needle pointed end thereof at said entry point and aligning a longitudinal axis of said instrument coaxially with said laser beam, said instrument being in no physical contact with said apparatus.

4. The method according to claim 3, wherein said step of aligning includes letting a distal end face of said instrument be pointed at by said laser beam.

5. The method according to claim 4, wherein said laser beam provides a light spot on said distal end face.

6. The method according to claim 4, wherein said laser beam provides a cross-hair like light image on said distal end face.

7. The method according to claim 3, further comprising positioning a laser carrying arm of said apparatus to lie horizontally above the body at right angles to said craniocaudal direction.

8. The method according to claim 7, wherein the positioning step includes using a line laser located on said laser carrying arm, said line laser providing a laser line, and aligning said laser line parallel to said craniocaudal direction.

9. The method according to claim 2, further comprising positioning a laser carrying arm of said apparatus to lie horizontally above the body at right angles to said craniocaudal direction.

10. The method according to claim 9, wherein the positioning step includes using a line laser located on said laser carrying arm, said line laser providing a laser line, and aligning said laser line parallel to said craniocaudal direction.

11. A method for assisting percutaneous computed tomography-guided surgical activity inside a human or animal body, said method for determining insertion depth, transverse insertion angle and craniocaudal insertion angle for a needle-type surgical instrument to be inserted into the human or animal body from an insertion entry point on a skin surface of said body to a target inside said body, comprising:

determining from a first tomography image first coordinate values for said entry point related to a first tomography slice position along craniocaudal direction, and horizontal and vertical directions transversely of said craniocaudal direction at said first position, determining from said first or a second tomography image second coordinate values for said target point related to said first or a second tomography slice position along craniocaudal direction, and horizontal and vertical directions transversely of said craniocaudal direction at said first or second position, calculating from said first and second coordinate values through principle of trigonometry values of said insertion depth, transverse insertion angle and craniocaudal insertion angle, applying said values of said transverse insertion angle and craniocaudal insertion angle to an instrument insertion guiding apparatus positioned adjacent to said body in no physical contact therewith, said apparatus having a laser which provides a laser beam, manipulating adjustment means on said apparatus to let said laser beam assume said values of transversal insertion angle and craniocaudal insertion angle and to let said laser beam point at said entry point, and locating said instrument with a needle pointed end thereof at said entry point and aligning a longitudinal axis of said instrument coaxially with said laser beam, said instrument being in no physical contact with said apparatus, wherein:
said step of aligning includes letting a distal end face of said instrument be pointed at by said laser beam, and said laser beam provides a cross hair-like light image on said distal end face.

12. The method according to claim 11, further comprising positioning a laser carrying arm of said apparatus to lie horizontally above the body at right angles to said craniocaudal direction.

13. The method according to claim 12, wherein the positioning step includes using a line laser located on said laser carrying arm, said line laser providing a laser line, and aligning said laser line parallel to said craniocaudal direction.

14. A method for assisting percutaneous computed tomography-guided surgical activity inside a human or animal body, said method for determining insertion depth, transverse insertion angle and craniocaudal insertion angle for a needle-type surgical instrument to be inserted into the human or animal body from an insertion entry point on a skin surface of said body to a target inside said body, comprising:
determining from a first tomography image first coordinate values for said entry point related to a first tomography slice position along craniocaudal direction, and horizontal and vertical directions transversely of said craniocaudal direction at said first position,
determining from a second tomography image second coordinate values for said target point related to a second tomography slice position along craniocaudal direction, and horizontal and vertical directions transversely of said craniocaudal direction at said second position,
calculating from said first and second coordinate values through principle of trigonometry values of said insertion depth, transverse insertion angle and craniocaudal insertion angle,
said transverse insertion angle value, said craniocaudal insertion angle value, said first coordinate values, and said second coordinate values defining a direction of insertion and insertion depth from said entry point,
applying said values of said transverse insertion angle and craniocaudal insertion angle to an instrument insertion guiding apparatus positioned adjacent to said body in no physical contact therewith, said apparatus having a laser which provides a laser beam, manipulating adjustment means on said apparatus to let said laser beam assume said values of transversal insertion angle and craniocaudal insertion angle and to let said laser beam point at said entry point, and
locating said instrument with a needle pointed end thereof at said entry point and aligning a longitudinal axis of said instrument coaxially with said laser beam, said instrument being in no physical contact with said apparatus,
wherein:
said step of aligning includes letting a distal end face of said instrument be pointed at by said laser beam, and said laser beam provides a light spot on said distal end face.

15. The method according to claim 14, further comprising positioning a laser carrying arm of said apparatus to lie horizontally above the body at right angles to said craniocaudal direction.

16. The method according to claim 15, wherein the positioning step includes using a line laser located on said laser carrying arm, said line laser providing a laser line, and aligning said laser line parallel to said craniocaudal direction.

17. A method for assisting percutaneous computed tomography-guided surgical activity inside a human or animal body, said method for determining insertion depth, transverse insertion angle and craniocaudal insertion angle for a needle-type surgical instrument to be inserted into the human or animal body from an insertion entry point on a skin surface of said body to a target inside said body, comprising:
determining from a first tomography image first coordinate values for said entry point related to a first tomography slice position along craniocaudal direction, and horizontal and vertical directions transversely of said craniocaudal direction at said first position,
determining from a second tomography image second coordinate values for said target point related to a second tomography slice position along craniocaudal direction, and horizontal and vertical directions transversely of said craniocaudal direction at said second position,
calculating from said first and second coordinate values through principle of trigonometry values of said insertion depth, transverse insertion angle and craniocaudal insertion angle,
said transverse insertion angle value, said craniocaudal insertion angle value, said first coordinate values, and said second coordinate values defining a direction of insertion and insertion depth from said entry point,
applying said values of said transverse insertion angle and craniocaudal insertion angle to an instrument insertion guiding apparatus positioned adjacent to said body in no physical contact therewith, said apparatus having a laser which provides a laser beam, manipulating adjustment means on said apparatus to let said laser beam assume said values of transversal insertion angle and craniocaudal insertion angle and to let said laser beam point at said entry point,
locating said instrument with a needle pointed end thereof at said entry point and aligning a longitudinal axis of said instrument coaxially with said laser beam, said instrument being in no physical contact with said apparatus,
wherein:
said step of aligning includes letting a distal end face of said instrument be pointed at by said laser beam, and said laser beam provides a cross hair-like light image on said distal end face.

18. The method according to claim 17, further comprising positioning a laser carrying arm of said apparatus to lie horizontally above the body at right angles to said craniocaudal direction.

19. The method according to claim 18, wherein the positioning step includes using a line laser located on said laser carrying arm, said line laser providing a laser line, and aligning said laser line parallel to said craniocaudal direction.

20. A method for assisting percutaneous computed tomography-guided surgical activity inside a human or animal body, said method for determining insertion depth, transverse insertion angle and craniocaudal insertion angle for a needle-type surgical instrument to be inserted into the human or animal body from an insertion entry point on a skin surface of said body to a target inside said body, comprising:

determining from a first tomography image first coordinate values for said entry point related to a first tomography slice position along craniocaudal direction, and horizontal and vertical directions transversely of said craniocaudal direction at said first position, determining from said first or a second tomography image second coordinate values for said target point related to said first or a second tomography slice position along craniocaudal direction, and horizontal and vertical directions transversely of said craniocaudal direction at said first or second position, calculating from said first and second coordinate values through principle of trigonometry values of said insertion depth, transverse insertion angle and craniocaudal insertion angle, applying said values of said transverse insertion angle and craniocaudal insertion angle to an instrument insertion guiding apparatus positioned adjacent to said body in no physical contact therewith, said apparatus having a laser which provides a laser beam, manipulating adjustment means on said apparatus to let said laser beam assume said values of transversal insertion angle and craniocaudal insertion angle and to let said laser beam point at said entry point, locating said instrument with a needle pointed end thereof at said entry point and aligning a longitudinal axis of said instrument coaxially with said laser beam, said instrument being in no physical contact with said apparatus, and positioning a laser carrying arm of said apparatus to lie horizontally above the body at right angles to said craniocaudal direction, wherein the positioning step includes using a line laser located on said laser carrying arm, said line laser providing a laser line, and aligning said laser line parallel to said craniocaudal direction.

21. A method for assisting percutaneous computed tomography-guided surgical activity inside a human or animal body, said method for determining insertion depth, transverse insertion angle and craniocaudal insertion angle for a needle-type surgical instrument to be inserted into the human or animal body from an insertion entry point on a skin surface of said body to a target inside said body, comprising:

determining from a first tomography image first coordinate values for said entry point related to a first tomography slice position along craniocaudal direction, and horizontal and vertical directions transversely of said craniocaudal direction at said first position, determining from a second tomography image second coordinate values for said target point related to a second tomography slice position along craniocaudal direction, and horizontal and vertical directions transversely of said craniocaudal direction at said second position, calculating from said first and second coordinate values through principle of trigonometry values of said insertion depth, transverse insertion angle and craniocaudal insertion angle, said transverse insertion angle value, said craniocaudal insertion angle value, said first coordinate values, and said second coordinate values defining a direction of insertion and insertion depth from said entry point, applying said values of said transverse insertion angle and craniocaudal insertion angle to an instrument insertion guiding apparatus positioned adjacent to said body in no physical contact therewith, said apparatus having a laser which provides a laser beam, manipulating adjustment means on said apparatus to let said laser beam assume said values of transversal insertion angle and craniocaudal insertion angle and to let said laser beam point at said entry point in said defined insertion direction, locating said instrument with a needle pointed end thereof at said entry point and aligning a longitudinal axis of said instrument coaxially with said laser beam, said instrument being in no physical contact with said apparatus, and positioning a laser carrying arm of said apparatus to lie horizontally above the body at right angles to said craniocaudal direction, wherein the positioning step includes using a line laser located on said laser carrying arm, said line laser providing a laser line, and aligning said laser line parallel to said craniocaudal direction.

* * * * *